(12) United States Patent
Burkholz et al.

(10) Patent No.: US 10,583,269 B2
(45) Date of Patent: Mar. 10, 2020

(54) MAGNETIZED CATHETERS, DEVICES, USES AND METHODS OF USING MAGNETIZED CATHETERS

(71) Applicant: Becton, Dickinson and Company, Franklin Lakes, NJ (US)

(72) Inventors: Jonathan Karl Burkholz, Salt Lake City, UT (US); Ming Zhou, Draper, UT (US); Siddarth Shevgoor, Sandy, UT (US); Marc W. Weimer, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 760 days.

(21) Appl. No.: 15/170,505

(22) Filed: Jun. 1, 2016

(65) Prior Publication Data
US 2017/0348509 A1    Dec. 7, 2017

(51) Int. Cl.
*A63F 9/24* (2006.01)
*A61M 25/01* (2006.01)
*A61B 5/06* (2006.01)
*A61B 8/08* (2006.01)
*A61M 25/00* (2006.01)
(Continued)

(52) U.S. Cl.
CPC ......... *A61M 25/0127* (2013.01); *A61B 5/062* (2013.01); *A61B 8/0841* (2013.01); *A61M 25/0097* (2013.01); *A61M 25/0108* (2013.01); *A61M 25/0606* (2013.01); *A61M 25/0618* (2013.01); *A61M 39/0247* (2013.01); *A61M 2039/0202* (2013.01); *A61M 2039/027* (2013.01); *A61M 2039/0258* (2013.01); *A61M 2039/0273* (2013.01); *A61M 2039/0276* (2013.01)

(58) Field of Classification Search
CPC ..... A61B 5/6852; A61B 5/062; A61B 8/0841; A61M 25/0127; A61M 25/0108; A61M 25/0606; A61M 25/0618
See application file for complete search history.

(56) References Cited

U.S. PATENT DOCUMENTS

| 4,161,943 A | 7/1979 | Nogier |
| 5,000,912 A | 3/1991 | Bendel et al. |
| 5,154,179 A | 10/1992 | Ratner |

(Continued)

FOREIGN PATENT DOCUMENTS

| EP | 0320623 A1 | 11/1988 |
| EP | 2730306 A1 | 5/2014 |

(Continued)

OTHER PUBLICATIONS

PCT IPRP in S/N PCT/US2017/033988, dated Dec. 4, 2018, 8 pgs.
(Continued)

*Primary Examiner* — Steve Rowland
(74) *Attorney, Agent, or Firm* — Servilla Whitney LLC

(57) ABSTRACT

Catheters, vascular access devices using such catheters, methods of using such catheters and uses of such catheters are disclosed. The catheter comprises polymeric tubing including a composition that can be magnetized by application of an externally applied magnetic field, thereby magnetizing the tubing. Detection of the magnetic field provides location information for the catheter in the vasculature.

29 Claims, 7 Drawing Sheets

(51) Int. Cl.
*A61M 25/06* (2006.01)
*A61M 39/02* (2006.01)

(56) References Cited

U.S. PATENT DOCUMENTS

| | | | |
|---|---|---|---|
| 5,215,528 A | 6/1993 | Purdy et al. | |
| 5,359,992 A | 11/1994 | Hori et al. | |
| 5,431,640 A | 7/1995 | Gabriel | |
| 5,558,651 A | 9/1996 | Crawford et al. | |
| 5,728,079 A | 3/1998 | Weber et al. | |
| 5,817,017 A | 10/1998 | Young et al. | |
| 6,171,297 B1* | 1/2001 | Pedersen | A61M 25/008 604/264 |
| 6,216,026 B1* | 4/2001 | Kuhn | A61B 5/06 600/409 |
| 6,216,029 B1 | 4/2001 | Paltieli | |
| 6,337,627 B1 | 1/2002 | Von Gutfeld et al. | |
| 6,432,036 B1 | 8/2002 | Kim | |
| 6,537,232 B1 | 3/2003 | Kucharczyk et al. | |
| 6,733,458 B1 | 5/2004 | Steins et al. | |
| 7,932,718 B1 | 4/2011 | Wiegert | |
| 7,935,080 B2 | 5/2011 | Howell et al. | |
| 8,388,541 B2 | 3/2013 | Messerly et al. | |
| 2002/0042581 A1 | 4/2002 | Cervi | |
| 2002/0052546 A1 | 5/2002 | Frantz et al. | |
| 2003/0100829 A1* | 5/2003 | Zhong | A61L 29/18 600/424 |
| 2003/0117135 A1* | 6/2003 | Martinelli | A61B 90/36 324/301 |
| 2004/0167506 A1 | 8/2004 | Chen | |
| 2004/0249428 A1 | 12/2004 | Wang et al. | |
| 2005/0004417 A1 | 1/2005 | Nelson et al. | |
| 2005/0027198 A1* | 2/2005 | Couvillon, Jr. | A61B 8/12 600/466 |
| 2005/0096589 A1* | 5/2005 | Shachar | A61B 1/00158 604/95.01 |
| 2005/0165301 A1 | 7/2005 | Smith et al. | |
| 2005/0203333 A1 | 9/2005 | Dailey et al. | |
| 2005/0215885 A1* | 9/2005 | Lee | A61F 2/95 600/420 |
| 2006/0264914 A1 | 11/2006 | Furst et al. | |
| 2007/0016006 A1* | 1/2007 | Shachar | A61B 1/00158 600/424 |
| 2007/0088197 A1* | 4/2007 | Garibaldi | A61B 1/00158 600/114 |
| 2007/0167747 A1* | 7/2007 | Borgert | A61B 17/12022 600/427 |
| 2007/0255211 A1 | 11/2007 | Young | |
| 2008/0006280 A1 | 1/2008 | Aliberto et al. | |
| 2008/0132911 A1 | 6/2008 | Sobe | |
| 2008/0204004 A1 | 8/2008 | Anderson | |
| 2008/0237367 A1 | 10/2008 | McNichols et al. | |
| 2008/0281391 A1* | 11/2008 | MacAdam | A61B 5/042 607/122 |
| 2009/0012517 A1 | 1/2009 | De La Rama et al. | |
| 2009/0032499 A1 | 2/2009 | Tenne et al. | |
| 2010/0036238 A1 | 2/2010 | Neidert et al. | |
| 2010/0217275 A1 | 8/2010 | Carmeli et al. | |
| 2010/0228119 A1 | 9/2010 | Brennan et al. | |
| 2010/0230862 A1 | 9/2010 | Arney et al. | |
| 2010/0305402 A1* | 12/2010 | Shachar | A61B 1/00158 600/118 |
| 2011/0092870 A1 | 4/2011 | Jarrell | |
| 2011/0196397 A1 | 8/2011 | Frantz et al. | |
| 2012/0041297 A1 | 2/2012 | McGary | |
| 2012/0046664 A1 | 2/2012 | McGuckin, Jr. et al. | |
| 2012/0143029 A1 | 6/2012 | Silverstein et al. | |
| 2013/0023758 A1* | 1/2013 | Fabro | A61B 1/00078 600/424 |
| 2013/0075649 A1 | 3/2013 | Wang | |
| 2013/0123704 A1 | 5/2013 | Bierman et al. | |
| 2013/0131547 A1 | 5/2013 | Hardert et al. | |
| 2013/0263668 A1 | 10/2013 | Hyun et al. | |
| 2014/0046261 A1 | 2/2014 | Newman et al. | |
| 2014/0107475 A1 | 4/2014 | Cos et al. | |
| 2014/0187916 A1* | 7/2014 | Clark | A61B 5/6885 600/424 |
| 2014/0187917 A1* | 7/2014 | Clark | A61B 5/062 600/424 |
| 2014/0253270 A1 | 9/2014 | Nicholls et al. | |
| 2014/0256708 A1 | 9/2014 | Dunbar et al. | |
| 2014/0257080 A1 | 9/2014 | Dunbar et al. | |
| 2014/0276539 A1 | 9/2014 | Allison et al. | |
| 2014/0296694 A1 | 10/2014 | Jaworski | |
| 2015/0080710 A1 | 3/2015 | Henkel et al. | |
| 2015/0320977 A1 | 11/2015 | Vitullo et al. | |
| 2015/0359991 A1 | 12/2015 | Dunbar et al. | |
| 2017/0232204 A1 | 8/2017 | Knapp et al. | |
| 2017/0325713 A1 | 11/2017 | Burkholz et al. | |
| 2017/0325714 A1* | 11/2017 | Sonderegger | A61B 5/0035 |
| 2017/0326342 A1 | 11/2017 | Ma et al. | |
| 2017/0347913 A1 | 12/2017 | Isaacson et al. | |
| 2017/0347914 A1 | 12/2017 | Isaacson et al. | |
| 2017/0348510 A1 | 12/2017 | Shevgoor et al. | |
| 2017/0348511 A1 | 12/2017 | Burkholz et al. | |

FOREIGN PATENT DOCUMENTS

| | | |
|---|---|---|
| WO | 02/083208 A2 | 10/2002 |
| WO | 2009061860 A1 | 5/2009 |
| WO | 2011069525 A1 | 6/2011 |
| WO | 2013/034175 A1 | 3/2013 |
| WO | 2013142386 A1 | 9/2013 |
| WO | 2014052894 A2 | 4/2014 |
| WO | 2016187456 A1 | 11/2016 |

OTHER PUBLICATIONS

PCT International Search Report and Written Opinion in PCT/US2017/033988 dated Aug. 24, 2017, 17 pages.
"Ferrite Toroids [online].", Magnetics, Sep. 1, 2010 [retrieved on Oct. 16, 2018]. Retrieved from the Internet: w <URL: https://web.archive.org/web/20100901184145/https://www.mag-inc.com/Products/Ferrite-Cores/Ferrite-Toroids>.
Nave, R. , "Ferromagnetism [online], Georgia State University, HyperPhysics, Jul. 1, 2006 [retrieved on Oct. 12, 2018],", Retrieved from the Internet: <URL: https://web,archive.org/web/20060701023036/http://hyperphysics.phyastr.gsu.edu/hbase/Solids/ferro.html>, 1 page.
Final Office Action in U.S. Appl. No. 15/154,348 dated Mar. 22, 2019, 9 pages.
Final Office Action in U.S. Appl. No. 15/154,353 dated Jul. 12, 2019, 12 pages.
Final Office Action in U.S. Appl. No. 15/170,497 dated Sep. 16, 2019, 47 pages.
"Laser Welding in Medical Device Technology [online],", Rofin, May 8, 2015 [retrieved on Jan. 26, 2019]. Retrieved from the Internet<URL: https://web.archive.org/web/20150508080208/https://www.rofin.com/en/rnarkets/medical-device-technology/laser-welding/>.
Non-Final Office Action in U.S. Appl. No. 15/154,348 dated Jun. 7, 2018, 14 pages.
Non-Final Office Action in U.S. Appl. No. 15/154,353 dated Mar. 19, 2019, 12 pages.
Non-Final Office Action in U.S. Appl. No. 15/170,531 dated Sep. 6, 2019, 41 pages.
Honnegowda, Lakshmisha , et al., "Security Enhancement for Magnetic Data Transaction in Electronic Payment and Healthcare Systems [online]", IACSIT International Journal of Engineering and Technology, Apr. 2013 [retrieved on Sep. 5, 2019], vol. 5, No. 2.
Non-Final Office Action in U.S. Appl. No. 15/604,244 dated Jun. 27, 2019, 50 pages.
PCT International Preliminary Report on Patentability & Written Opinion in PCT/US2017/034515, dated Dec. 4, 2018, 8 pgs.
PCT International Preliminary Report on Patentability & Written Opinion in PCT/US2017/034517, dated Aug. 2, 2017, 15 pgs.
PCT International Search Report in PCT/US2017/031572 dated Aug. 24, 2017, 14 pages.

(56) References Cited

OTHER PUBLICATIONS

PCT International Search Report and Written Opinion in PCT/US2017/034515 dated Aug. 2, 2017, 15 pages.
PCT International Preliminary Report on Patentability in PCT/US2017/031566 dated Nov. 22, 2018, 11 pages.
PCT International Preliminary Report on Patentability in PCT/US2017/031572 dated Nov. 22, 2018, 8 pages.
PCT International Preliminary Report on Patentability in PCT/US2017/033984 dated Dec. 13, 2018, 9 pages.
PCT International Search Report and Written Opinion in PCT/US2017/033986 dated Aug. 28, 2017, 17 pages.
PCT International Search Report and Written Opinion in PCT/US2017/031569 dated Aug. 28, 2017, 17 pages.
PCT International Search Report and Written Opinion in PCT/US2017/033984, dated Aug. 2, 2017, 15 pgs.
PCT International Search Report and Written Opinion in PCT/US2017/033985 dated Sep. 25, 2017, 16 pages.

\* cited by examiner

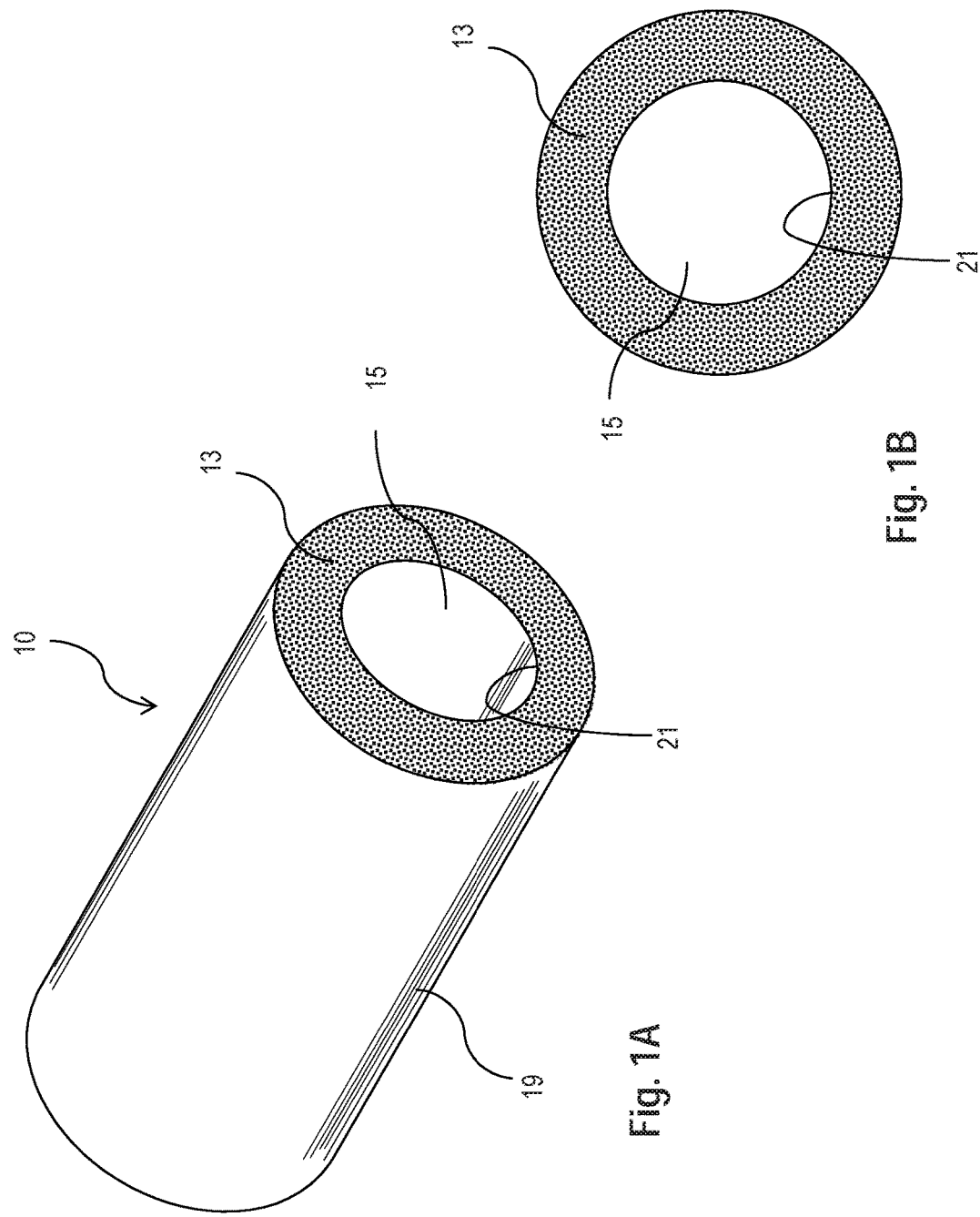

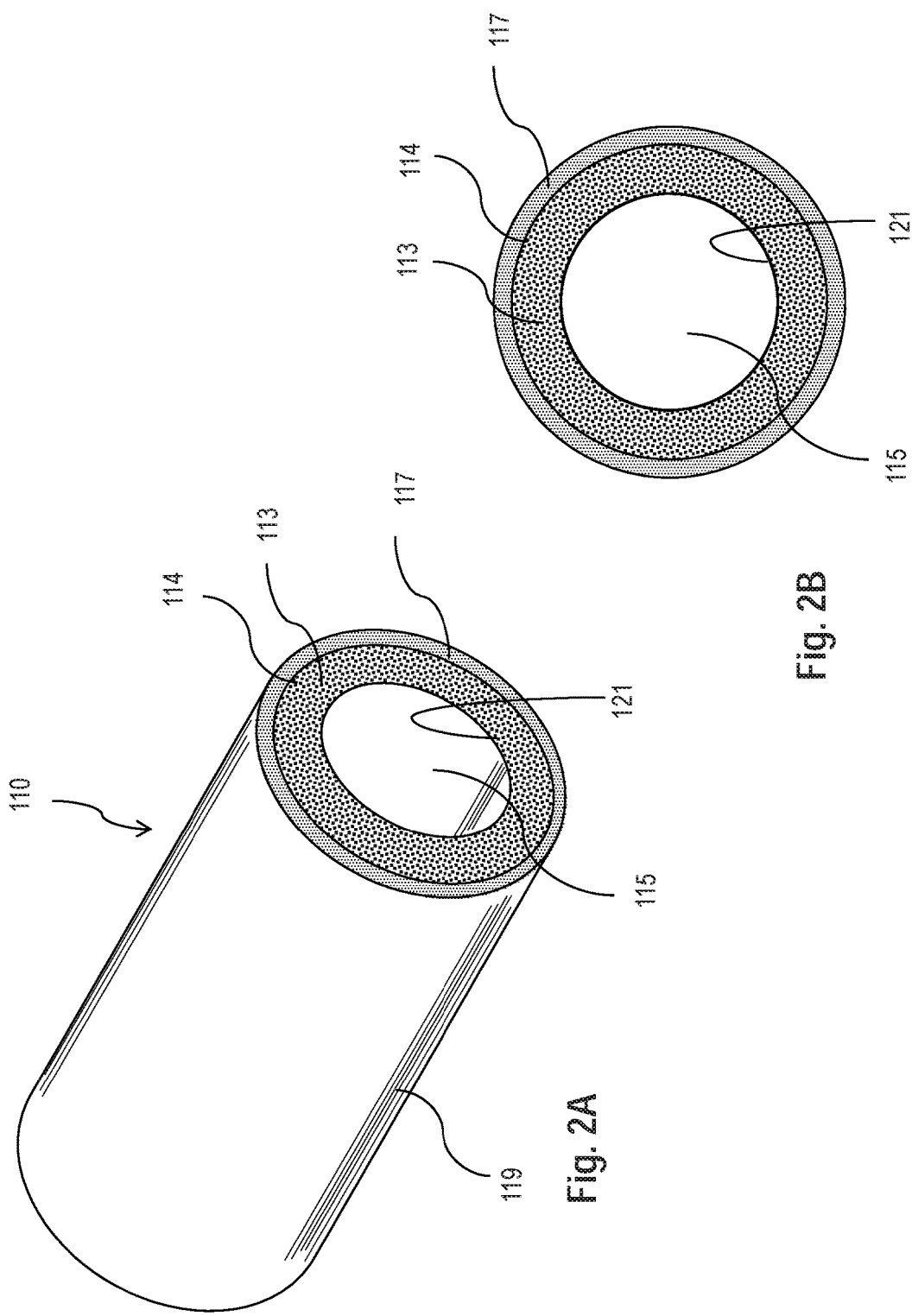

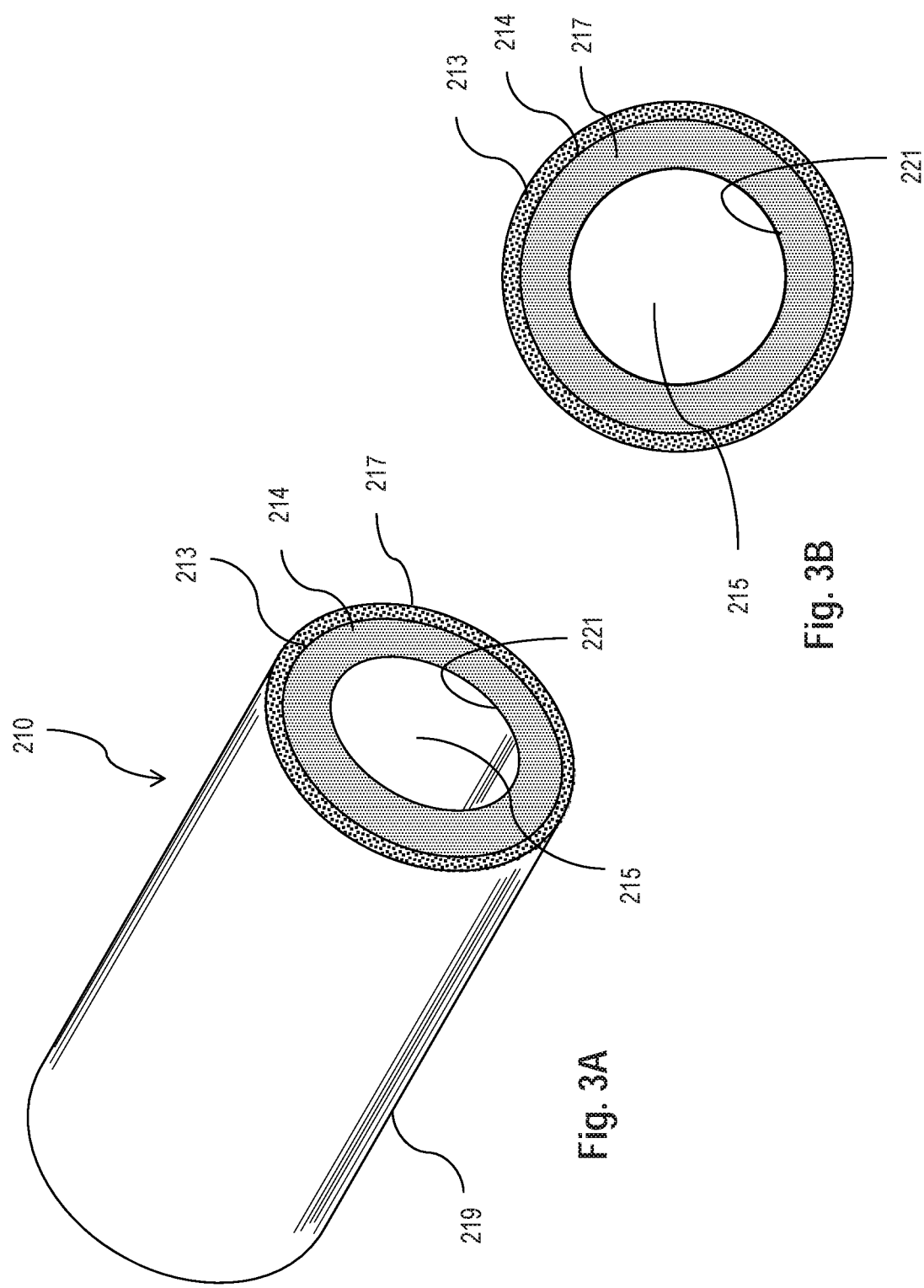

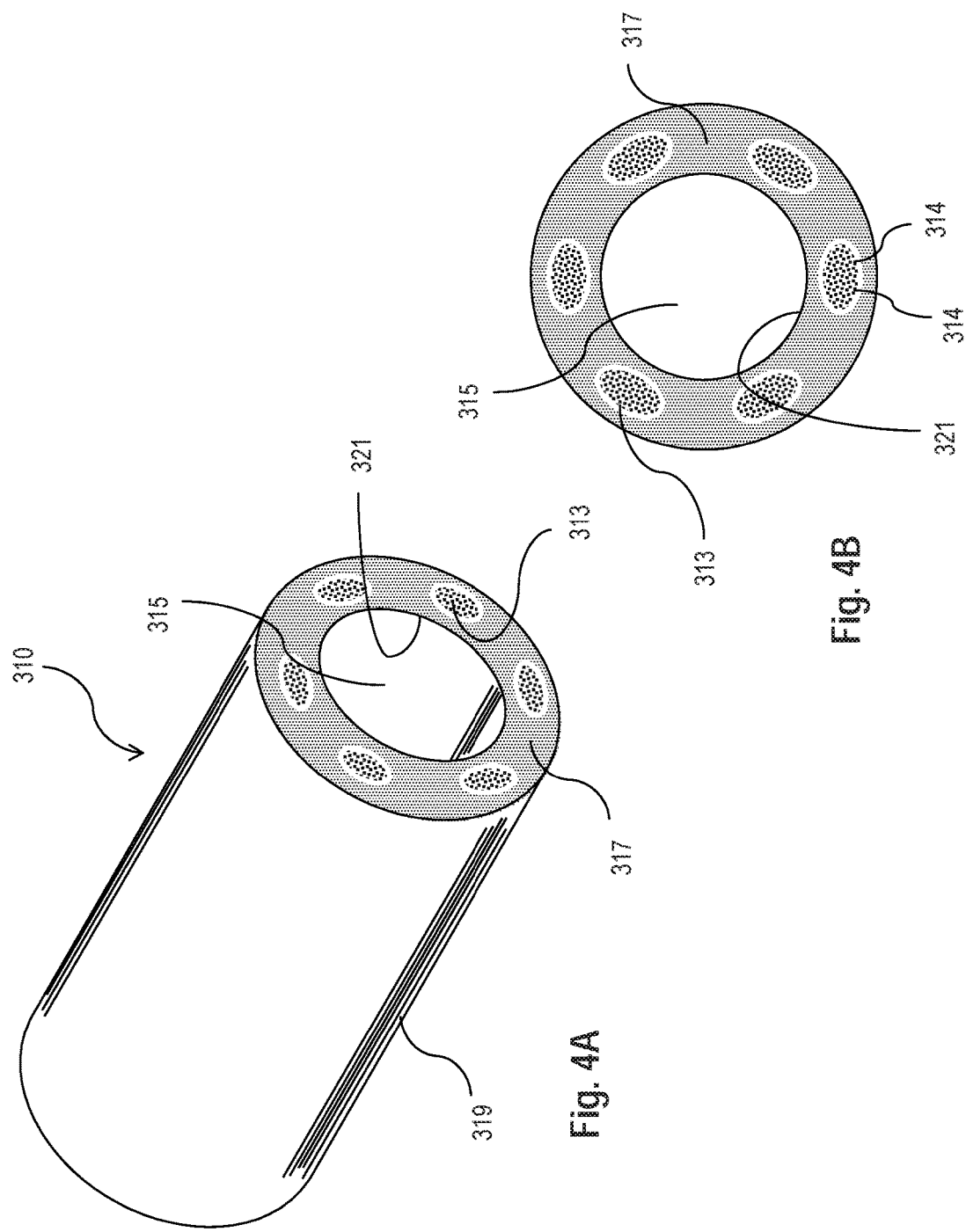

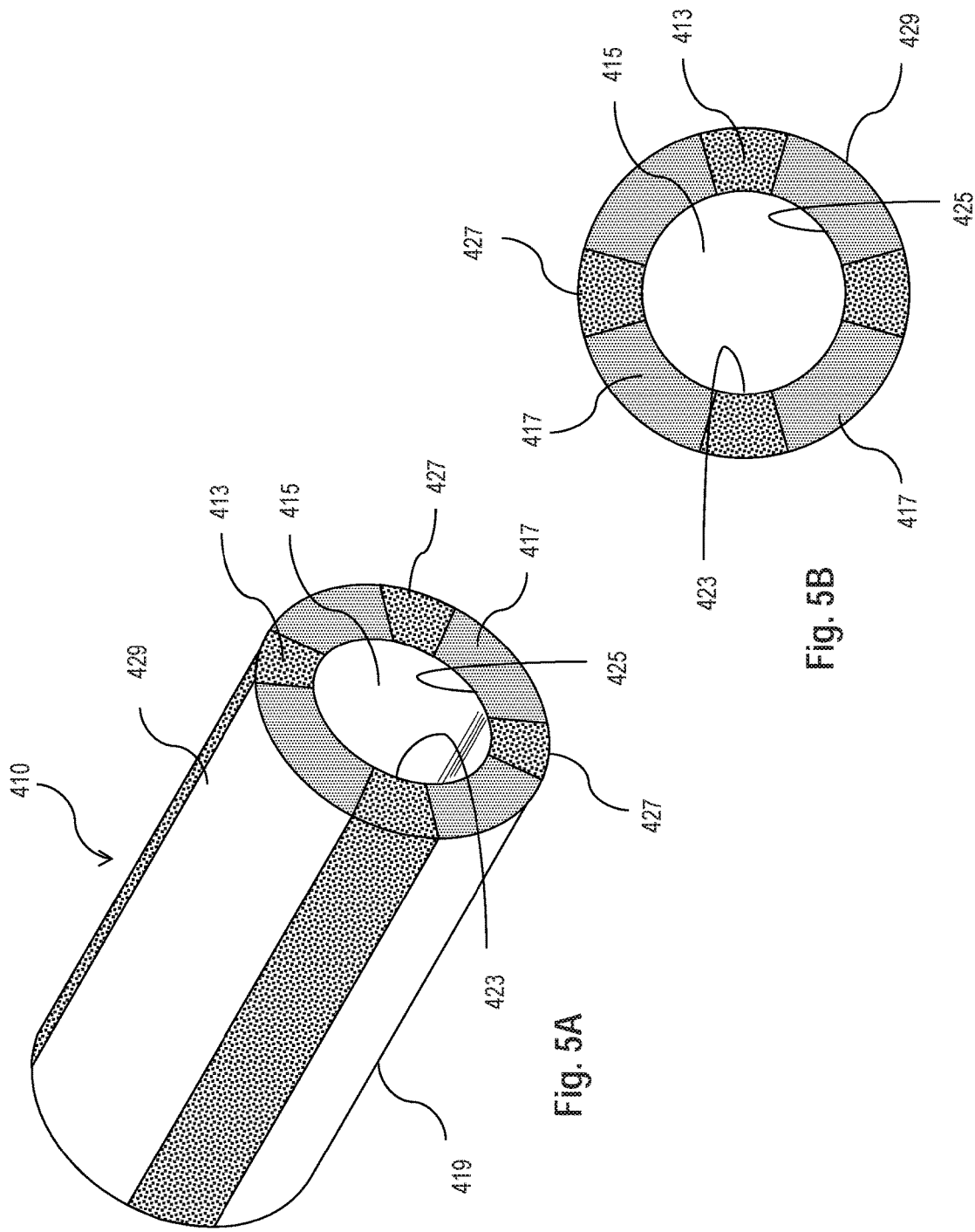

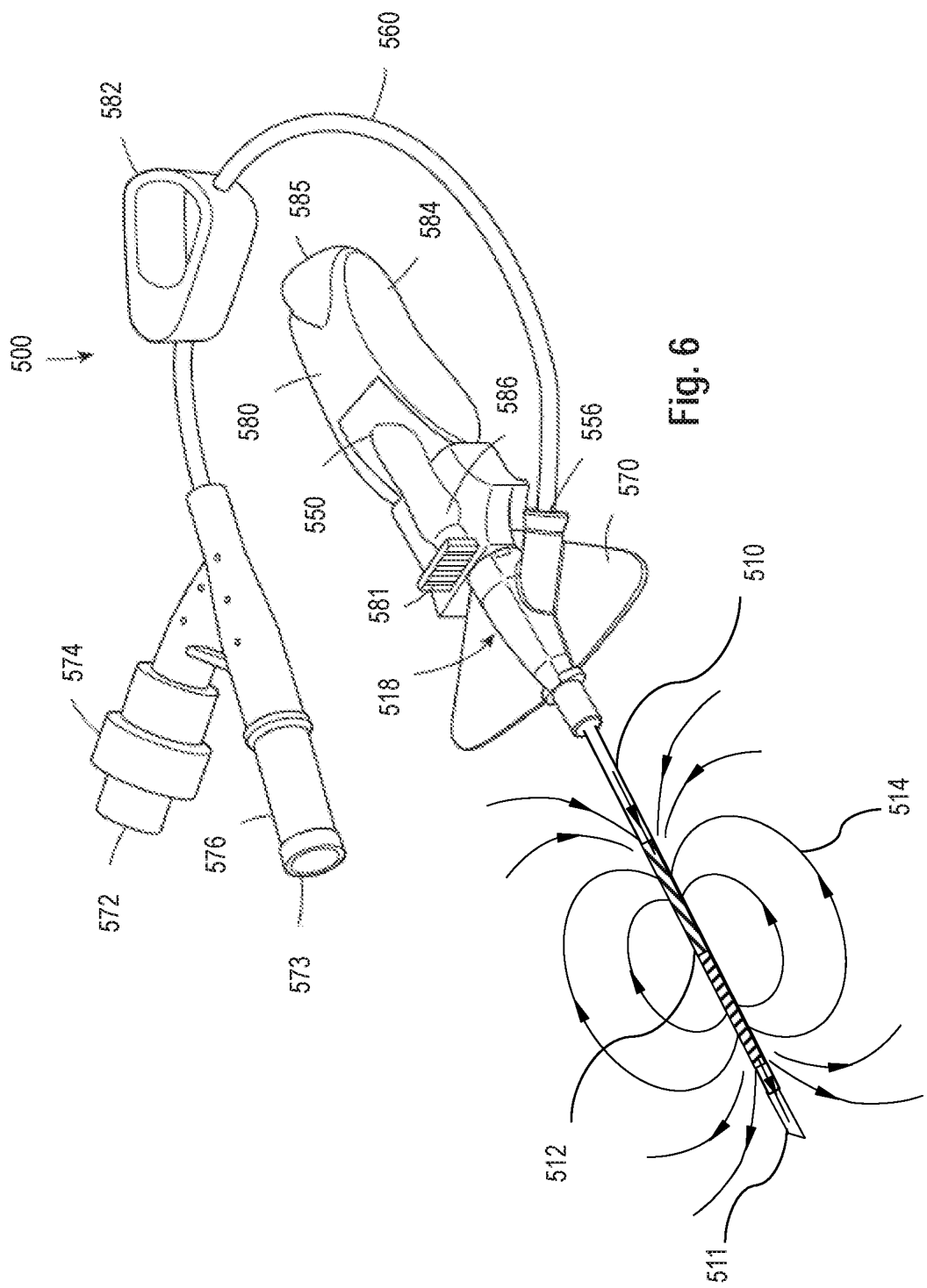

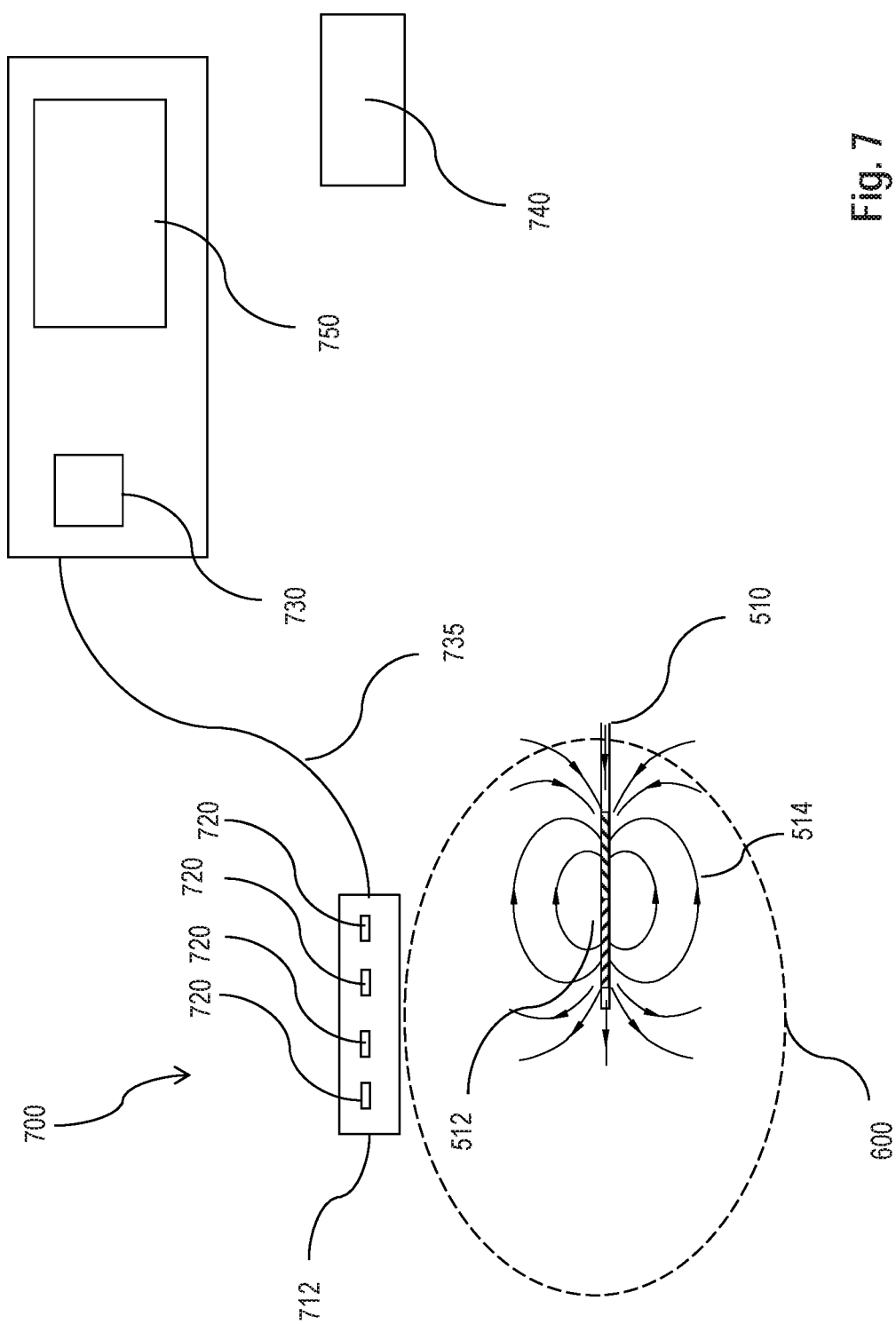

MAGNETIZED CATHETERS, DEVICES, USES AND METHODS OF USING MAGNETIZED CATHETERS

TECHNICAL FIELD

The present disclosure relates to a magnetized polymeric catheter which provides enhanced visualization of a vascular access device during an invasive insertion procedure. Such catheters can be used in medical devices, systems and methods for visualization of the catheter when combined with ultrasound technologies to provide visualization of sub-dermal anatomy and device position in the in-plane and out-of-plane orientation, and allow for projection or anticipation of the position of the insertion device relative to the patient's anatomy, thereby improving the likelihood of successfully accessing the vasculature.

BACKGROUND

Traditionally, penetration of a needle and catheter tubing through skin tissue to reach the vein during catheter insertion is invisible to clinicians. For this reason, they must rely on their first-hand experience with needle insertion in combination with tactile sense to successfully identify the location of the vein. This may be a difficult task when attempting to access a small vein in a deep location under the skin, increasing risk of excess pain and/or injury to the patient.

Procedural guidance systems for enhancing visualization of an invasive procedure rely on an invasive device having a magnetic field source. This can be achieved by embedding a magnet in a known position on the device, or by using an externally applied magnetic field to magnetize a portion of the invasive device prior to insertion. The portion of the invasive device that is targeted for magnetization is typically the metal cannula used during insertion of the invasive device.

For vascular access devices, magnetizing the metal cannula has significant limitations because this approach does not provide precise location information for the catheter tip relative to the vascular anatomy. It is therefore difficult to ensure that the catheter is properly inside the vein prior to cannula removal. Further, once the cannula is removed the guidance system can no longer be used to determine the location of the catheter tubing throughout the indwell period of the device. It would be desirable to provide catheters that could be used with devices, systems and methods to provide improved visualization of catheters and medical devices.

SUMMARY

One aspect of the disclosure relates to a catheter comprising polymeric material, wherein at least a portion of the polymeric tubing comprises a magnetized composition which has been magnetized by an externally applied magnetic field, the magnetized composition comprising a magnetic material dispersed in the polymer. In certain embodiments, the magnetic composition is dispersed in the polymeric material, which forms the tubing. In a specific embodiment, the magnetized composition comprises an inner layer surrounding the lumen of the catheter with an outer layer of non-magnetizable polymeric material, for example, polymer. In an alternative specific embodiment, the layer of magnetized composition is an outer layer surrounding an inner layer of non-magnetizable polymer. In one or more embodiments, the magnetized composition forms longitudinal segments of the catheter separated by longitudinal segments of non-magnetizable polymeric material.

In any of the foregoing embodiments of the catheter, the magnetized composition may further comprise a radiopaque component. Alternatively, in any of the foregoing embodiments, a non-magnetized portion of catheter may comprise a radiopaque component.

Another aspect is directed to a vascular access device comprising the polymeric catheter according to any of the foregoing embodiments. In a specific embodiment, the vascular access device is a peripheral intravenous catheter insertion device or a syringe which includes the polymeric catheter having the magnetized portion and a needle cannula disposed within the polymeric catheter, the magnetized portion of the polymeric catheter having a magnetic field that is detectable by a magnetometer.

A further aspect is directed to methods for locating a catheter, for example, a polymeric catheter, inserted in a patient's vasculature, wherein the method comprises: a) magnetizing a catheter according to any of the foregoing embodiments to provide a magnetized catheter with a known magnetic field at a selected distance through tissue of known permeability; b) measuring strength and direction of the magnetic field produced by the inserted catheter using a magnetometer outside the patient's body; and c) determining the location of the catheter based on the measured strength and direction and a correlation between the known magnetic field at the selected distance and the tissue permeability. In one or more embodiments, the methods further comprise detecting placement of a needle or cannula contained within the catheter using an ultrasound imaging system prior to locating the polymeric catheter.

Another aspect is directed to use of a magnetized catheter, for example, a polymeric catheter, for locating a catheter within a patient's vasculature, wherein the catheter may be as set forth in any of the foregoing embodiments of the catheter, and wherein strength and direction of a magnetic field produced by the catheter in the patient's vasculature is measured using a magnetometer outside the patient's body. In one or more embodiments, the use further comprises detecting placement of a needle or cannula contained within the catheter using an ultrasound imaging system prior to locating the polymeric catheter.

BRIEF DESCRIPTION OF THE DRAWINGS

FIG. 1A is a perspective view of a catheter according to an embodiment;

FIG. 1B is an end view of the catheter of FIG. 1A;

FIG. 2A is a perspective view of a catheter according to an embodiment;

FIG. 2B is an end view of the catheter of FIG. 2A;

FIG. 3A is a perspective view of a catheter according to an embodiment;

FIG. 3B is an end view of the catheter of FIG. 3A;

FIG. 4A is a perspective view of a catheter according to an embodiment;

FIG. 4B is an end view of the catheter of FIG. 4A.

FIG. 5A is a perspective view of a catheter according to an embodiment;

FIG. 5B is an end view of the catheter of FIG. 5A;

FIG. 6 is a perspective view of a vascular access device according to an embodiment; and FIG. 7 is a schematic view of an ultrasound system according to an embodiment.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

Embodiments of the present disclosure provide catheters which can be used with a variety of vascular access devices and in various methods and systems. In one or more embodiments, the catheters comprise material, for example, polyurethane, which includes a magnetizable component. In one or more embodiments, the catheters and vascular access devices can be utilized with an ultrasound imaging system so that the catheter can be tracked and visualized in real time. In one or more embodiments, insertion of a metal cannula within the catheter comprising a magnetized component enables ultrasound guided needle placement, which permits visualization of the insertion process and location of the position of both the cannula and the vein to improve success rates of needle insertion on the first attempt. The location of the magnetized catheter or device can be determined using magnetometers to determine the strength of the magnetic field and its direction. According to one or more embodiments, catheter tubing remains visible by imaging systems after the cannula is removed so that additional adjustment of the tubing in the vein can be undertaken if needed.

One aspect relates to a catheter comprising polymeric tubing, wherein at least a portion of the polymeric tubing comprises a magnetized composition which has been magnetized by an externally applied magnetic field prior to insertion of the catheter tubing into a patient, the magnetized composition comprising a magnetic material dispersed in the polymer. One such embodiment is shown in FIGS. 1A and 1B. With reference to FIGS. 1A and 1B a catheter 10, which can comprise polymeric tubing, at least a portion of the catheter 10 including a magnetized composition 13 comprising a magnetic material dispersed in the catheter material, which may be a polymer. The magnetized composition 13 has been magnetized by an externally applied magnetic field prior to insertion of the catheter into a patient. In the embodiment shown, a catheter 10 is defined by elongate tubing having an outer surface 19 and an inner surface 21 which surrounds the magnetized composition 13 dispersed in the polymer and defines lumen 15.

In a specific embodiment illustrated in FIGS. 2A and 2B, the magnetized composition 113 is provided in a magnetized inner layer 114 surrounding lumen 115 of catheter 110, which can comprise polymeric tubing with a non-magnetizable outer layer 117, which can comprise non-magnetizable polymer. In this embodiment, the lumen 115 of the catheter 110 defined by polymeric tubing providing the magnetized inner layer 114 comprising magnetizable composition 113 dispersed in the polymer, and the non-magnetizable outer layer 117 of the catheter 110 is non-magnetizable. Thus, catheter 110 thus includes a non-magnetizable outer surface 119, and a magnetized inner surface 121.

In another specific embodiment illustrated in FIGS. 3A and 3B, magnetized composition 213 is in a magnetized outer layer 217 of catheter 210, which can comprise polymeric tubing, surrounding a non-magnetizable inner layer 214. In this embodiment, lumen 215 of the catheter 210 is surrounded by the non-magnetizable inner layer 214 comprising non-magnetizable polymer and the magnetized outer layer 217 comprises a magnetized composition 213 dispersed in polymer. Thus, catheter 210 provides a magnetized outer surface 219, and a non-magnetizable inner surface 221.

In one or more alternative embodiments, a magnetized composition forms longitudinal segments or "stripes" on or in a catheter separated by longitudinal non-magnetizable segments, which can be comprised of a polymer. In a specific embodiment illustrated in FIGS. 4A and 4B, magnetized longitudinal segments 313 comprising magnetized composition are surrounded non-magnetizable segments 317 providing an inner surface 321 and an outer surface 319 of catheter 310 comprising polymeric tubing. In one or more embodiment, each magnetized longitudinal segment 313 comprising magnetized composition is surrounded by non-magnetizable segments 317 within the wall of the catheter 310. In an alternative embodiment, the magnetized longitudinal segments 317 can include elongate magnetized elements, for example, elongate magnetized wires 314 that can be co-formed (e.g., co-extruded) with the catheter tubing, and the magnetized wires 314 can be magnetized by an applied external magnetic field prior to insertion of the catheter into a patient. In the embodiment shown, in FIG. 4B, a plurality of magnetized wires 314 is shown in each longitudinal segment 313. Other configurations are possible, in which fewer wires are included in each longitudinal segment 313, or even a single magnetized wire 314 is provided in the longitudinal segment. Thus, lumen 315 of catheter 310 is surrounded by non-magnetized polymer, providing an inner surface 321, which is non-magnetizable, and the outer surface 319 which is non-magnetizable. Magnetization of this catheter results in longitudinal magnetized "stripes" or longitudinal magnetized segments within the wall of the catheter 310.

In yet another specific embodiment illustrated in FIGS. 5A and. 5B, a catheter 410 comprises magnetized longitudinal segments 413 comprising magnetized composition extending from an inner surface to an outer surface 419 of the catheter 410, which may be comprised of polymeric tubing defining a lumen 415. Such a structure provides corresponding magnetized inner surface 423 and magnetized outer surface 427 of catheter 410. The magnetized longitudinal segments 427 are separated by non-magnetizable longitudinal segments 417, which can comprise a polymer, which provide corresponding non-magnetizable inner surface 425 and non-magnetizable outer surface 429 of the catheter 410 separating magnetized longitudinal segments 427.

In any of the foregoing embodiments of the catheter described with respect to FIGS. 1A-B through 5A-B, the magnetized composition or the magnetized portion of the catheter may further comprise a radiopaque component or radiopaque material. According to the various embodiments described herein, the radiopaque component or radiopaque material may be uniformly dispersed in the material that comprises the tubing, which in one or more embodiments, comprises a polymer. By way of example, the magnetized portion of the catheter may comprise a radiopaque component. A radiopaque component is not transparent to radiation and is visible in x-ray photographs and/or under fluoroscopy. According to one or more embodiments, a radiopaque component is selected from, for example, barium sulfate, bismuth subcarbonate, bismuth oxychloride, bismuth trioxide, tungsten and mixtures thereof.

Alternatively, in any of the foregoing embodiments of the catheter, a non-magnetizable portion of the polymeric tubing may comprise a radiopaque component. According to the various embodiments described herein, the radiopaque component may be dispersed in an inner non-magnetizable layer of the material that forms the catheter. Alternatively, the radiopaque component may be dispersed in an outer non-magnetizable layer of the material that forms the catheter. In other embodiments, the radiopaque component can be dispersed in longitudinal non-magnetizable segments of the material that forms the catheter. In embodiments in which the non-magnetizable portion of the polymeric tubing comprises a radiopaque component, the radiopaque component may be selected from, for example, barium sulfate, bismuth subcarbonate, bismuth oxychloride, bismuth trioxide, tungsten and mixtures thereof.

In any of the foregoing embodiments, magnetic components or magnetic materials are added to polymeric materials that form catheters (for example, silicone rubber, nitinol, nylon, polyurethane, fluoroethylene polymer (FEP), polytetrafluoroethylene polymer (PTFE), polyethylene terephthalate (PET), latex, and thermoplastic elastomers) to provide a composition that is magnetized when a magnetic component or magnetic material is added to the polymeric material and a magnetic field is applied to magnetize the composition. In any of the foregoing embodiments, the magnetic material in the magnetized composition may be selected from powdered iron, magnetic iron oxide, magnetic titanium oxide, magnetic powdered steel, magnetic iron alloys, paramagnetic or ferromagnetic compounds containing chromium, magnesium, or molybdenum, and mixtures thereof. In a specific embodiment, the magnetic iron alloy is an alloy including nickel, zinc, and/or copper. In other specific embodiments, the magnetic material is selected from ferrites and rare earths, such as Neodymium-Iron-Boron, and Samarium-Cobalt. Anisotropic powders of ferrites have excellent cost/performance ratio, and low electrical resistance. Rare earths have higher magnetic performances, service temperatures, electrical resistance and cost.

In any of the foregoing embodiments, the magnetic material in the magnetized composition may be in the range of 1% to 15% (w/w) of the material that forms the catheter. In a specific embodiment, the magnetic material in the magnetized composition is in the range of 1% to 10% (w/w) of the material that forms the catheter. In a further specific embodiment, the magnetic material in the magnetized composition is in the range of 0.5% to 5% (w/w) material that forms the catheter. The magnetic component or magnetic material imparts a low level of magnetic susceptibility without substantially changing original physical properties of virgin resin or molded part. The size and thickness of polymer or elastomer part, density of virgin material, and the type of virgin material can also influence how much additive is required to get desired detectable signals.

Magnetic components or magnetic materials can be compounded into polymers or elastomers during manufacturing to slightly magnetize the polymers or elastomers to render them magnetically susceptible and detected by metal detectors or x-ray systems. Such magnetic components or magnetic materials may be paramagnetic or ferromagnetic. The magnetic polymers can be further magnetized or polarized during molding as a secondary operation. Non-limiting examples of magnetic components or magnetic materials are provided above. For medical devices in contact with the body, toxicity of the additive is also a consideration, and therefore, paramagnetic or ferromagnetic elements or compounds that contain essential metals such as chromium, magnesium, molybdenum, etc. may also be used. For instance chromium, an essential metal and strongly ferromagnetic, may be compounded in powder form into polymer and extruded to form catheter tubes.

Another aspect is directed to a vascular access device comprising the catheter according to any of the foregoing embodiments. The vascular access device comprises a catheter which is sized and configured to be placed into a peripheral vein for administration of medication or fluids to a patient. After insertion, the catheter can also be used to draw blood. Such vascular access devices typically include a metal needle (cannula) within the polymeric catheter to facilitate placement of the catheter in the vasculature. The cannula is then withdrawn, leaving the catheter in place. The present disclosure provides an additional option or an alternative to magnetizing the metal cannula of the vascular access device. According to one or more embodiments, a magnetized catheter remains in the patient's vasculature for long-term detection of location, whereas when the metal cannula is removed, after placement of the catheter, ability to detect the location of the cannula is lost. According to one or more embodiments, a vascular access device may be a central venous catheter, a peripheral inserted central catheter, a peripheral intravenous cannula, an arterial catheter, or a mid-line catheter.

An exemplary embodiment of a vascular access device 500 including a catheter according to any of the foregoing embodiments described with respect to FIGS. 1A-B through 5A-B is illustrated in FIG. 6. The vascular access device 500 shown in FIG. 6 comprises a catheter adapter 518 and a polymeric catheter 510 comprising a magnetized feature 512 includes magnetized composition comprising a magnetized material as described herein. Magnetized portion 512 is magnetized by application of an externally applied magnetic field. Magnetizing the magnetized portion 512 of polymeric catheter 510 with an externally applied magnetic field creates a magnetic field 514 in the region of magnetized portion 512. Magnetic field 514 is remains detectable after removal of a needle cannula 511 from polymeric catheter 510 after placement in a patient.

The vascular access device 500 may include a lateral access port 556 and may be connected to a section of an extension tube 560 for establishing fluid communication between an IV fluid source and the polymeric catheter 510. In one or more embodiments, the extension tube 560 is built-in to reduce contamination and mechanical phlebitis by eliminating manipulation at the insertion site. In one or more embodiments, the extension tube 560 is compatible with high pressure injection. In one or more embodiments, the extension tube 560 provides continuous confirmation of vessel access during advancement of the catheter into the patient vein.

In one or more embodiments, a needle of a needle hub assembly 550 is inserted into the lumen (not show) of the polymeric catheter 510. The needle hub assembly 550 is shown as including finger grips 584 positioned at the sides of the needle hub assembly 550 to facilitate various insertion techniques. In one or more embodiments, bumps may be present on the finger grip to indicate where to the user may grip the device for needle removal. In one or more embodiments, a thumb pad 585, having a gently convex surface, is provided at the proximal end of the needle hub assembly 550. A flange 586, having a gently convex surface, is provided at the proximal end of the hub assembly to provide a finger pad. A wing member 570, thumb pad 585 and flange 586 may be utilized by the user during insertion, permitting the user to elect which insertion technique to employ.

In one or more embodiments, the needle hub assembly 550 includes a needle shield 580. The needle shield 580 may be a design adapted to secure the tip of the needle within the shield after use. In one or more embodiments, the needle shield 580 may be activated passively. The needle tip is completely covered by the needle shield 580 in a fixed position. In one or more embodiments, a ferrule, crimp or other structure may be included near the tip for engagement with a needle shield in certain applications.

A push tab 581 may be provided to facilitate catheter advancement during insertion. The push tab 581 also allows for one-handed or two-handed advancement. In one or more embodiments, the push tab 581 is removed with the needle shield 580. A clamp 582 may also be included on the extension tubing to prevent blood flow when replacing the access port.

In one or more embodiments, the vascular access device 500 further includes a first luer access 572 and a second luer access 573 in fluid communication with the extension tube 560, a blood control split septum 574 associated with the first luer access 572, and an air vent 576 associated with the second luer access 573. Split septum 574 allows for a reduction in catheter-related bloodstream infection (CRBSI) while providing unrestricted flow and a straight fluid path and functions as a blood control septum. In one or more embodiments, the split septum 574 may be located in an internal cavity of the catheter adapter or on the distal end of the catheter adapter. In yet another embodiment, the split septum 574 may be located on a distal end of the extension tube 560. The air vent 576 allows air to escape from the system during insertion, providing continuous confirmation of vascular access while preventing leakage of blood from the system during insertion. In one or more embodiments, the air vent 576 may be at the distal end of extension tube 560.

The magnetic material may be compounded into the polymer in powder form during manufacturing to slightly magnetize the polymer and render the polymer magnetically susceptible. The magnetic material may be paramagnetic or ferromagnetic. Alternatively, the magnetic material may comprise elongate magnetizable elements, such as magnetizable wire that can be co-formed with the tubing, for example, such as during an extrusion process. The magnetic material of the magnetized polymer may be further magnetized or polarized during molding as a secondary operation. Wetting agents and emulsifiers, or combinations thereof, may be used to form stable dispersions with ferromagnetic particles during manufacture of the polymeric tubing.

The polymer resins useful according to embodiments of the disclosure may be fabricated into tubing by conventional thermoplastic fabricating techniques including solution casting, extrusion molding, etc. The resin may have incorporated therein, as desired, conventional stabilizers and other additives. The amounts of these materials will vary depending upon the application of the polymer, but they are typically present in amounts ranging from about 0.2 to 50 weight percent of the polymer.

Another aspect of the disclosure pertains to methods for locating a catheter inserted in a patient's vasculature, wherein the method comprises: a) magnetizing a polymeric catheter according to any of the foregoing embodiments to provide a magnetized polymeric catheter with a known magnetic field at a selected distance through tissue of known permeability; b) measuring strength and direction of the magnetic field produced by the inserted polymeric catheter using a magnetometer outside the patient's body; and c) determining the location of the polymeric catheter based on the measured strength and direction and a correlation between the known magnetic field at the selected distance and the tissue permeability. In one or more embodiments, the methods further comprise detecting placement of a needle contained within the polymeric catheter using an ultrasound imaging system prior to locating the polymeric catheter.

The location of the magnetized catheter/vascular access device can be accomplished by using magnetometers to determine the strength of the magnetic field and its direction. If an invasive catheter or vascular access device is magnetized to produce a known magnetic field B at a given distance x through tissue of permeability $\mu r$, then a mathematical correlation between the two i.e. $x=f(B, \mu_r)$ can be derived. According to an embodiment, three different magnetometers are arranged in a three-dimensional grid array, orthogonal to each other are used, and a three-dimensional (3D) correlation can be derived where $I=f(B_i \mu_r)$, where $i=x$ or y or z along three axes. Such correlation can be extended to an array of 3-dimensional (3D) magnetometers to obtain the precise distance to the magnetized catheter or vascular access device from the array of 3D magnetometers. If the location of the array of 3D magnetometers is known in reference to the ultrasound sensor, then the precise location of the magnetized device with respect to the ultrasound sensor can be calculated. An inferred image of the device can then be created and superimposed over the ultrasound image and displayed. An exemplary magnetic sensing method using magnetometers and a lookup table instead of a mathematical function to determine the location of a magnetized invasive device from the magnetic field strength measured outside the body using magnetometers is shown and described in United States Patent Application Publication Number US20140257080. The method described in US20140257080 can be adapted as described herein, for example, a three-dimensional (3D) correlation is from a mathematical function, and the correlation is extended to an array of 3-dimensional (3-D) magnetometers, one of the magnetometers outside the patient's body, to obtain the precise distance to the magnetized catheter or vascular access device from the array of 3D magnetometers. Another exemplary method of referencing the magnetometers with respect to an ultrasound probe is described in PCT Patent Application Publication Number WO2013034175, which can be adapted as described herein. For example, as shown in FIG. 7, an ultrasound system 700 is shown including a polymeric catheter 510 comprising a magnetized portion 512 includes magnetized composition comprising a magnetized material as described herein is shown inside of a patient's body 600. A magnetometric detector 712 comprising an array of magnetometers 720 (which can be housed in a probe of an ultrasound system, not shown) can be used to detect the magnetic field 514 from the polymeric catheter 510 together with the terrestrial magnetic field and any other background magnetic field. The magnetometric detector 712 is in communication with an ultrasound processor 730 adapted to determine from the detected field the position and orientation of the polymeric catheter 510 relative to the magnetometric detector 712. This magnetically detected position is then displayed on a display 750 together with the ultrasound image.

The ultrasound system 700 can be a standard two dimensional B-mode ultrasound system with a standard ultrasound probe modified by the provision of the magnetometric detector 712. The ultrasound processor 730, which can be connected to the ultrasound probe via a cable 735, sends electrical signals to the magnetometric detector 712 to cause it to generate ultrasound pulses and interpreting the raw data received from the transducer probe housing the magnetometric detector 712, which represents echoes from the patient's body, to assemble it into an image of the patient's tissue.

The magnetometric detector 712 can be attached to the ultrasound probe and can be battery powered or powered from the ultrasound system. In specific embodiments, positioning elements are provided on the magnetometric detector 712 to ensure that it is always attached in the same well-defined position and orientation. The magnetometric detector 712 can connected by a wireless connection to a base unit 740 which is in wireless or wired (e.g. USB) communication with the ultrasound processor 730 and the display 750. The base unit 740 can be integrated with, or some of its functions performed by, the ultrasound processor 730 or the magnetometric detector 712.

The base unit 740 receives normalized measurements from magnetometric detector 712 and calculates the position, or optionally the position and orientation, of the polymeric catheter 510. The base unit 740 can also receive additional information such as the state of charge of the magnetometric detector's battery and information can be sent from the base unit 740 to the magnetometric detector 712, such as configuration information. The base unit 740 forwards the results of its calculations, i.e. the position and, optionally, orientation, to the ultrasound processor 730 for inclusion in the displayed ultrasound image of an image of the polymeric catheter 510.

In one or more embodiments, the base unit 740 can be integrated into the ultrasound system 700 with the ultrasound processor 730 and the magnetometric detector 712 being in direct communication with the ultrasound system 700 either via wireless link or using the same physical cable 735.

Thus, in one or more embodiments, the magnetized composition is magnetized prior to insertion of the catheter into a patient using any suitable device to magnetize a needle or medical device to produce a magnetic field B at a distance x through tissue of permeability $\mu$, and the correlation is calculated as $x=f(B, \mu_r)$. Similar correlations can be calculated for the y axis, z axis and for relative angular movement $\omega$, for example, $y=f(B, \mu_r)$, $z=f(B, \mu_r)$ and $\omega=f(B, \mu_r)$. In one or more embodiments, three magnetometers 720 are placed orthogonally to each other are used to derive a 3-dimensional correlation $I=f(B_i, \mu_r)$, wherein i=x or y or z along three axes. In a specific embodiment, the distance from the magnetized polymeric catheter to the 3-dimensional array of magnetometers is calculated. In a further specific embodiment, location of the array of magnetometers in reference to an ultrasound sensor of an ultrasound imaging system is used to calculate a location of the polymeric catheter with respect to the ultrasound sensor. In another specific embodiment, the method comprises displaying an image of the polymeric catheter superimposed over an ultrasound image of the needle.

Another aspect of the disclosure is directed to use of a magnetized polymeric catheter for locating the catheter within a patient's vasculature, wherein the catheter may be as set forth in any of the foregoing embodiments, and wherein strength and direction of a magnetic field produced by the polymeric catheter in the patient's vasculature is measured using a magnetometer outside the patient's body. In one or more embodiments, the use further comprises detecting placement of a needle contained within the polymeric catheter using an ultrasound imaging system prior to locating the polymeric catheter. In a specific embodiment, the use further comprises displaying an image of the polymeric catheter superimposed over an ultrasound image of the needle.

The catheters described herein can be used in a variety of medical procedures, including, but not limited to, vascular access, regional anesthesia, minimally-invasive surgical procedures, fine needle aspiration, detection of bio-electrical signals, and musculoskeletal injections. Thus, the catheters described herein can be utilized in any procedure where it is desired to guide a medical device to a desired position in a patient's body and/or to monitor or track the medical device position to ensure that it remains at the desired location.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A catheter comprising polymer tubing, wherein at least a portion of the polymeric tubing comprises a magnetized portion which has been magnetized by an externally applied known magnetic field to produce a magnetic field B at a distance x through tissue of permeability $\mu$ so that a location of the catheter is detectable by a magnetometer based on a measured strength and direction of the known magnetic field and a correlation between the known magnetic field at the selected distance and the tissue permeability, the correlation calculated as $x=f(B, \mu_r)$.

2. The catheter according to claim 1, wherein the magnetized portion includes a magnetized composition comprising a magnetic material dispersed in a polymer.

3. The catheter according to claim 2, wherein the wherein the magnetized composition forms a magnetized layer on the polymeric tubing is a magnetized outer layer surrounding a non-magnetizable inner layer.

4. The catheter according to claim 1, wherein the magnetized portion further comprises a radiopaque component.

5. The catheter according to claim 4, wherein the radiopaque component is selected from the group consisting of barium sulfate, bismuth subcarbonate, bismuth oxychloride, bismuth trioxide, tungsten and mixtures thereof.

6. The catheter according to claim 3, wherein the magnetized composition further comprises a radiopaque component selected from the group consisting of barium sulfate, bismuth subcarbonate, bismuth oxychloride, bismuth trioxide, tungsten and mixtures thereof.

7. The catheter according to claim 1, wherein the magnetized portion forms magnetized longitudinal segments between an inner surface and an outer surface of the tubing, wherein the magnetized longitudinal segments are separated by longitudinal non-magnetizable segments.

8. The catheter according to claim 7, wherein the magnetized portion comprises a magnetized composition.

9. The catheter according to claim 7, wherein the magnetized portion comprises magnetized wires co-formed with the polymeric tubing.

10. The catheter according to claim 7, wherein the magnetized portion further comprises a radiopaque component.

11. The catheter according to claim 10, wherein the radiopaque component is selected from the group consisting of barium sulfate, bismuth subcarbonate, bismuth oxychloride, bismuth trioxide, tungsten and mixtures thereof.

12. The catheter according to claim 2, wherein the magnetic material is dispersed uniformly within the at least a portion of the polymer.

13. The catheter according to claim 1, wherein the magnetized portion forms magnetized longitudinal segments between an inner surface and an outer surface of the catheter and the magnetized longitudinal segments are separated by non-magnetizable longitudinal segments comprising a radiopaque material.

14. The catheter according to claim 2, wherein the magnetic material is selected from the group consisting of powdered iron; magnetic iron oxide; magnetic titanium oxide; magnetic powdered steel; magnetic iron alloys; paramagnetic or ferromagnetic compounds containing one of chromium, magnesium, and molybdenum; and mixtures thereof.

15. The catheter according to claim 14, wherein the magnetic iron alloy is an alloy with nickel, zinc, and/or copper.

16. The catheter according to claim 2, wherein the magnetic material in the magnetized composition is less than 15% (w/w) of the polymer.

17. The catheter according to claim 16, wherein the magnetic material in the magnetized composition is less than 10% (w/w) of the polymer.

18. The catheter according to claim 16, wherein the magnetic material in the magnetized composition is less than 5% (w/w) of the polymer.

19. A method for locating a catheter inserted in a patient's vasculature, the method comprising:
   a) magnetizing a polymeric catheter to provide a magnetized polymeric catheter, at least a portion of the catheter comprising a magnetized composition including a magnetic material dispersed in the polymer, with a known magnetic field, the magnetized composition magnetized to produce a magnetic field B at a distance x through tissue of permeability μ;
   b) measuring strength and direction of the known magnetic field produced by the polymeric catheter inserted in the patient's vasculature using a magnetometer outside the patient's body to obtain a measured strength and direction of the known magnetic field; and
   c) determining the location of the polymeric catheter based on the measured strength and direction and a correlation between the known magnetic field at the selected distance and the tissue permeability, the correlation calculated as $x=f(B, \mu_r)$.

20. The method according to claim 19, further comprising detecting placement of a needle contained within the polymeric catheter using an ultrasound imaging system prior to locating the polymeric catheter.

21. The method according to claim 19, wherein three magnetometers placed orthogonally to each other are used to derive a 3-dimensional correlation $I=f(B_i, \mu_r)$, wherein i=x or y or z along three axes.

22. The method according to claim 21, wherein the distance from the magnetized polymeric catheter to an array of 3-dimensional magnetometers is calculated.

23. The method according to claim 19, wherein a location of an array of magnetometers in reference to an ultrasound sensor of the ultrasound imaging system is used to calculate a location of the polymeric catheter with respect to the ultrasound sensor.

24. The method according to claim 23, further comprising displaying an image of the polymeric catheter superimposed over an ultrasound image of the needle.

25. Use of a magnetized polymeric catheter to determine a location of a polymeric catheter within a patient's vasculature, at least a portion of the polymeric catheter comprising a magnetized portion magnetized with a known magnetic field and including a magnetic material dispersed in a polymer, the magnetized portion magnetized to produce a magnetic field B at a distance x through tissue of permeability μ, and a measured strength and direction of the magnetic field produced by the polymeric catheter in the patient's vasculature is measured using a magnetometer outside the patient's body, the location of the polymeric catheter based a correlation between the known magnetic field at the selected distance and the tissue permeability, the correlation calculated as $x=f(B, \mu_r)$.

26. The use according to claim 25, further comprising detecting placement of a needle contained within the polymeric catheter using an ultrasound imaging system prior to locating the polymeric catheter.

27. The use according to claim 26, further comprising displaying an image of the polymeric catheter superimposed over an ultrasound image of the needle.

28. A vascular access device comprising the polymeric catheter according to claim 1.

29. The vascular access device according to claim 28, the polymeric catheter having a proximal end and a distal end, the device further comprising:
   a catheter adapter having a distal end, a proximal end, an overall length extending from the distal end to the proximal end, an internal cavity, an upper portion, a lower portion and a tip region having a distal opening having a circumference through which the polymeric catheter extends, the catheter adapter being connected to the proximal end of the polymeric catheter, and a needle cannula disposed with the polymeric catheter, the magnetized portion of the polymeric catheter having a magnetic field that is detectable by a magnetometer.

* * * * *